(12) United States Patent
Rohaly et al.

(10) Patent No.: US 7,646,550 B2
(45) Date of Patent: Jan. 12, 2010

(54) THREE-CHANNEL CAMERA SYSTEMS WITH COLLINEAR APERTURES

(75) Inventors: Janos Rohaly, Acton, MA (US); Douglas P. Hart, Charlestown, MA (US); Thomas J. Brukilacchio, Reading, MA (US)

(73) Assignee: 3M Innovative Properties Company, Saint Paul, MN (US)

( * ) Notice: Subject to any disclaimer, the term of this patent is extended or adjusted under 35 U.S.C. 154(b) by 639 days.

(21) Appl. No.: 11/530,420

(22) Filed: Sep. 8, 2006

(65) Prior Publication Data

US 2007/0188769 A1    Aug. 16, 2007

Related U.S. Application Data

(60) Provisional application No. 60/773,132, filed on Feb. 13, 2006.

(51) Int. Cl.
*G02B 9/08* (2006.01)
*H04N 15/00* (2006.01)
*H04N 5/225* (2006.01)
*G03B 35/00* (2006.01)

(52) U.S. Cl. .............. 359/740; 348/48; 348/218.1; 396/325

(58) Field of Classification Search ............ 348/47, 348/48, 218.1; 359/740; 396/324, 325, 335, 396/340
See application file for complete search history.

(56) References Cited

U.S. PATENT DOCUMENTS

| | | | |
|---|---|---|---|
| 5,076,687 A | 12/1991 | Adelson | |
| 5,270,795 A | 12/1993 | Blais | |
| 5,510,831 A | 4/1996 | Mayhew | |
| 5,608,529 A | 3/1997 | Hori | |
| 5,612,816 A | 3/1997 | Strahle et al. | |
| 5,625,435 A | 4/1997 | Lo et al. | |
| 5,659,429 A | 8/1997 | Kudo | |
| 5,671,449 A | 9/1997 | Shimizu | |
| 5,678,089 A | 10/1997 | Bacs et al. | |
| 5,699,112 A | 12/1997 | Bacs, Jr. | |
| 5,703,677 A | 12/1997 | Simoncelli et al. | |
| 5,743,847 A | 4/1998 | Nakamura et al. | |
| 5,784,847 A | 7/1998 | Wiklund | |
| 5,835,228 A | 11/1998 | Okazaki et al. | |
| 5,933,664 A | 8/1999 | Bacs | |
| 5,991,551 A | 11/1999 | Bacs et al. | |
| 6,005,716 A | 12/1999 | Ligtenberg et al. | |

(Continued)

FOREIGN PATENT DOCUMENTS

WO    WO 03/017000    2/2003

(Continued)

OTHER PUBLICATIONS

[5] Schechner, Y Y., et al., "Depth from Defocus vs. stereo: How different really are they?", *International Journal of Computer Vision 39(2):*, Kiryati N,(2000),141-162.

(Continued)

*Primary Examiner*—David N Spector
(74) *Attorney, Agent, or Firm*—Lance L Vietzke

(57) ABSTRACT

A three-dimensional imaging system uses a single primary optical lens along with three collinear apertures to obtain three offset optical channels each of which can be separately captured with an optical sensor.

23 Claims, 15 Drawing Sheets

U.S. PATENT DOCUMENTS

| | | | |
|---|---|---|---|
| 6,108,458 | A | 8/2000 | Hart |
| 6,115,059 | A | 9/2000 | Son et al. |
| 6,139,490 | A | 10/2000 | Breidenthal et al. |
| 6,271,918 | B2 | 8/2001 | Blais |
| 6,278,847 | B1 | 8/2001 | Gharib et al. |
| 6,282,028 | B1 | 8/2001 | Waibel et al. |
| 6,324,347 | B1 | 11/2001 | Bacs, Jr. et al. |
| 6,338,711 | B1 | 1/2002 | Sekiya et al. |
| 6,387,579 | B1 | 5/2002 | Vernackt |
| 6,522,473 | B2 | 2/2003 | Takeyama |
| 6,542,249 | B1 | 4/2003 | Kofman et al. |
| 6,618,558 | B2 | 9/2003 | Enomoto |
| 6,777,658 | B2 | 8/2004 | Atmur |
| 6,801,370 | B2 | 10/2004 | Sekiyama et al. |
| 6,807,295 | B1 | 10/2004 | Ono |
| 6,859,332 | B2 | 2/2005 | Nagata et al. |
| 6,877,865 | B2 | 4/2005 | English, Jr. et al. |
| 6,885,486 | B2 | 4/2005 | Kimura |
| 6,910,773 | B2 | 6/2005 | Nakashima et al. |
| 6,914,727 | B2 | 7/2005 | Karasawa |
| 6,921,169 | B2 | 7/2005 | Su et al. |
| 6,975,898 | B2 | 12/2005 | Seibel |
| 7,006,132 | B2 | 2/2006 | Pereira et al. |
| 7,372,642 | B2 | 5/2008 | Rohaly et al. |
| 2002/0111740 | A1 | 8/2002 | Horvath et al. |
| 2002/0149691 | A1 | 10/2002 | Pereira et al. |
| 2002/0171740 | A1 | 11/2002 | Seo |
| 2004/0119882 | A1 | 6/2004 | Maruno et al. |
| 2004/0155975 | A1 | 8/2004 | Hart et al. |
| 2005/0069188 | A1 | 3/2005 | Rubbert et al. |
| 2007/0188601 | A1 | 8/2007 | Rohaly et al. |
| 2007/0188769 | A1 | 8/2007 | Rohaly et al. |
| 2007/0195162 | A1 | 8/2007 | Graff et al. |
| 2008/0013943 | A1 | 1/2008 | Rohaly et al. |
| 2008/0204900 | A1* | 8/2008 | Rohaly et al. ............... 359/740 |

OTHER PUBLICATIONS

Ares, J , et al., "Position and displacement sensing with Shack Hartmann wave-front sensors", *Applied Optics*, 39(10):, Mancebo T; Bara S,(2000),1511-1520.

Blais, F , et al., "BIRIS: A simple 3-D sensor.", *Proc. SPIE—Optics, Illumination, and Image Sensing for Machine Vision*, 728., Publ by SPIE, Bellingham, WA, USA,(1986),235-242.

Castellini, C , et al., "Hartmann test modification for measuring ophthalmic progressive lenses", *Applied Optics 33(19)*:, Francini F, and Tribilli B,(Jul. 1994),4120-4124.

Hart, D P., "High-speed PIV analysis using compressed image correlation", *Journal of Fluids Engineering, Transactions of the ASME 120(3)*:, (1998),563-470.

Hart, D P., "PIV error correction", *Experiments in Fluids 29(1)*:, (2000),13-22.

Hart, D P., "Super-resolution PIV through recursive local-correlation", *VSJ-SPIE International Conference on Optical Technology and Image Processing in Fluid, Thermal, and Combustion Flow,*, Yokohama, Japan,(Dec. 6-10, 1998).

Laude, V, et al., "Hartmann wave-front scanner", *Optics Letters 24(24)*, Olivier S, Dirson C, Huignard J-P,(Dec. 1999),1796-1798.

Malacara, D , et al., "Testing and centering of lenses by means of a Hartmann test with 4 holes", *Optical Engineering 31(7)*:, and Malacara Z,(Jul. 1992),1551-1555.

Mansell, J D., et al., "Focal plane position detection with a diffractive optic for Shack-Hartmann wave-front sensor fabrication", *Applied Optics-OT 40(7)*:, Gustafson E K,(Mar. 2001),1074-1079.

Olivier, S , et al., "Liquid-crystal Hartmann wave-front scanner", *Applied Optics-OT 39(22)*:, Laude V, Huignard J-P,(Aug. 2000),3838-3846.

Rohaly, J , et al., "High resolution, ultra fast 3-D imaging", *Proc. Three-Dimensional Image Capture and Applications III*, SPIE vol. 3958, Hart D P,(2000).

Rohaly, J , et al., "Monocular 3-D Active -PTV", *Proc. 4th International Symposium on Particle Image Velocimetry, Paper 1147*, Lammerding J, Frigerio F, and Hart D P Göttingen, Germany,(Sep. 17-19, 2001).

Rohaly, J , et al., "Monocular 3-D magnetic bead microrheometry", *Proc. 11th International Symposium on Applications of Laser Techniques to Fluid Mechanic*, Lammerding J, and Hart D P Lisbon, Portugal,(Jul. 8-11, 2002).

Rohaly, J , et al., "Reverse hierarchical PIV processing", *Meas. Sci. Technol. 13(7)*:, Frigerio F, and Hart D P,(2002),984-996.

Tan, S , et al., "A novel particle displacement measurement method using optical diffraction", *Meas. Sci. Technol. 13(7)*:, Hart D P,(2002),1014-1019.

Willert, C E., et al., "Three-dimensional particle imaging with a single camera.", *Experiments in Fluids 12*, Gharib M,(1992),353-358.

"U.S. Appl. No. 11/530,413, Non-Final Office Action mailed Dec. 5, 2008", 12 pgs.

"PCT International Search Report", *Search Report 1*, (Jul. 25, 2007),All Pages.

* cited by examiner

THREE-CHANNEL CAMERA SYSTEMS WITH COLLINEAR APERTURES

RELATED APPLICATIONS

This application claims the benefit of U.S. Application No. 60/773,132 filed on Feb. 13, 2006.

This application is also related to Ser. No. 12/279,097 entitled "MONOCULAR THREE-DIMENSIONAL IMAGING" and Ser. No. 11/530,420 entitled "THREE-CHANNEL CAMERA SYSTEMS WITH NON-COLLINEAR APERTURES".

Each of the above applications is incorporated herein by reference in its entirety.

BACKGROUND

1. Field of the Invention

This invention relates to the field of imaging, and more particularly to the field of pupil sampling for multi-view three-dimensional imaging.

2. Description of the Related Art

One approach to capturing three-dimensional depth information is the use of a pair of two-dimensional recording devices whose relative orientation is known. Much like human or animal optical systems, obtaining depth information from stereo optical systems is a triangulation technique that relies on the difference or disparity between the recorded positions of one or more target points on two imaging sensors. For each target feature, the magnitude of the disparity is directly related to that feature's distance from the imaging system. However, in machine vision systems this approach has shortcomings, such as the high cost of multiple camera/lens systems and the high computational cost of processing large target feature disparities between one sensor and another.

A closely related technology to stereo imaging is triplet imaging, where three separate images are used, rather than two. Triplet imaging is generally used to eliminate processing ambiguity and to provide imaging redundancy, thereby improving accuracy and robustness with minimal addition to computational cost. Most triplet imaging systems consist of three cameras placed equidistant from each other in the form of an equilateral triangle. Stereo systems usually take advantage of rectified camera position that results in disparity only in one direction. In this respect other triplet arrangements (such as an "L" configuration) may yield favorable results. Like stereo-based systems, objects appear displaced in each of the images acquired by these systems, with a displacement between cameras proportional to depth. However, unlike stereo systems, the object is displaced in both the horizontal and vertical directions among the three cameras. Once relative camera positions are known, image rectification can reduce the two-dimensional disparities into one-dimensional disparities. To resolve three-dimensional information, the disparity of object features appearing in the three images is determined through triangulation in much the same way as in stereo-based imaging. The three views define all points and edges (lines) within the imaged space. Using more than two sensors assists with working around the so-called "aperture effect" in imaging system, wherein local image disparity can only be determined perpendicular to the texture features providing the signal. This determination requires non-collinear sensors. Having more sensors also assists with occlusion of target surfaces, where one sensor is blocked, but the others can still provide sufficient information, the benefit of which is greater with non-collinear sensors.

In triangulation-based three-dimensional imaging systems (including stereo and triplet imaging systems), a need exists to accurately determine the displacement of object features between acquired images. The processing required to determine this displacement (and thereby allow distinct images to be resolved to a common coordinate system) is commonly referred to as image registration. Many types of image registration processing have been developed, including optical flow (based on the gradients of recorded image intensities), correlation (based on the spatial uniqueness of imaged object feature orientation and intensity), and graph cut (based on minimization of a user defined energy function relating image characteristics).

Thus, a number of mathematical and algorithmic techniques have been developed for resolving optical data into three-dimensional representations of imaged subject matter. However, there remains a need for improved optical trains to acquire data for three-dimensional imaging.

SUMMARY

A three-dimensional imaging system uses a single primary optical lens along with three collinear apertures to obtain three offset optical channels each of which can be separately captured with an optical sensor.

In one aspect, a device disclosed herein includes an aperture element positioned within a primary optical facility having a center axis, the aperture element including three apertures positioned collinearly, each one of the apertures selectively transmitting a portion of an optical wavefront of the primary optical facility, thereby providing three optical channels, and a center one of the apertures positioned on the center axis.

The three apertures may be substantially equally spaced apart. The aperture element may include one or more of a moving plate, an electronic aperture, a shutter, a shuttering aperture, an oscillating aperture, a flipping mirror, a rotating mirror, and a digital light processor. The aperture element may be adapted to rotate on the center axis. The device may include a refocusing facility having three refocusing elements located at conjugate positions to the three apertures within the primary optical facility. The refocusing facility may be adapted to rotate on the center axis. The aperture element may be adapted to rotate on the center axis. The refocusing facility may be adapted to rotate in an opposite direction from the aperture element. The device may include three optical sensors positioned to capture data from each of the three optical channels. Each one of the three optical sensors may include a collection of sensors to acquire RGB data. The device may include a sampling facility that redirects the three optical channels to the three optical sensors. The sampling facility may include two mirrors separated by a space that passes a center one of the optical channels corresponding to the center one of the apertures. The sampling facility may include three mirrors. The sampling facility may include at least one prism. The at least one prism may include a prism having a hole that passes a center one of the optical channels corresponding to the center one of the apertures.

In another aspect, a device disclosed herein includes a refocusing facility positioned within a primary optical facility having a center axis, the refocusing facility including three refocusing elements positioned collinearly and substantially equally spaced, each one of the three refocusing elements refocusing a portion of an optical wavefront of the primary optical facility, and a center one of the refocusing elements positioned on the center axis.

The refocusing facility may be adapted to rotate on the center axis. The refocusing elements may include at least one mirror. The refocusing elements may include at least one lens. The refocusing elements may include at least one meso-optical element. The device may include three optical sensors positioned to capture data from each of the three optical channels. Each one of the three optical sensors may include a collection of sensors to acquire RGB data.

In another aspect, a method of processing images from sensors disclosed herein includes receiving the output of three optical sensors of an imaging system, the three optical sensors including a center sensor that captures data from a center channel of an optical path and two side sensors, each side sensor having an equal displacement with respect to image motion within the optical path; changing a sign of displacement direction of a registration between two of the sensors; and combining a registration between the center sensor and the two side sensors.

All documents identified herein are incorporated by reference in their entirety.

BRIEF DESCRIPTION OF THE FIGURES

The invention and the following detailed description of certain embodiments thereof may be understood by reference to the following figures.

DETAILED DESCRIPTION

It will be understood that the ray traces and lenses depicted in the following figures are for purposes of illustration only, and depict optical paths generally in the disclosed systems. The ray traces and lens shapes should not be understood to limit the scope of the invention in any sense including the magnitude, direction, or focus of light rays or bundles passing through various optical components, notwithstanding any variations in number, direction, shape, position or size thereof, except as expressly indicated in the following detailed description.

Figure 1:
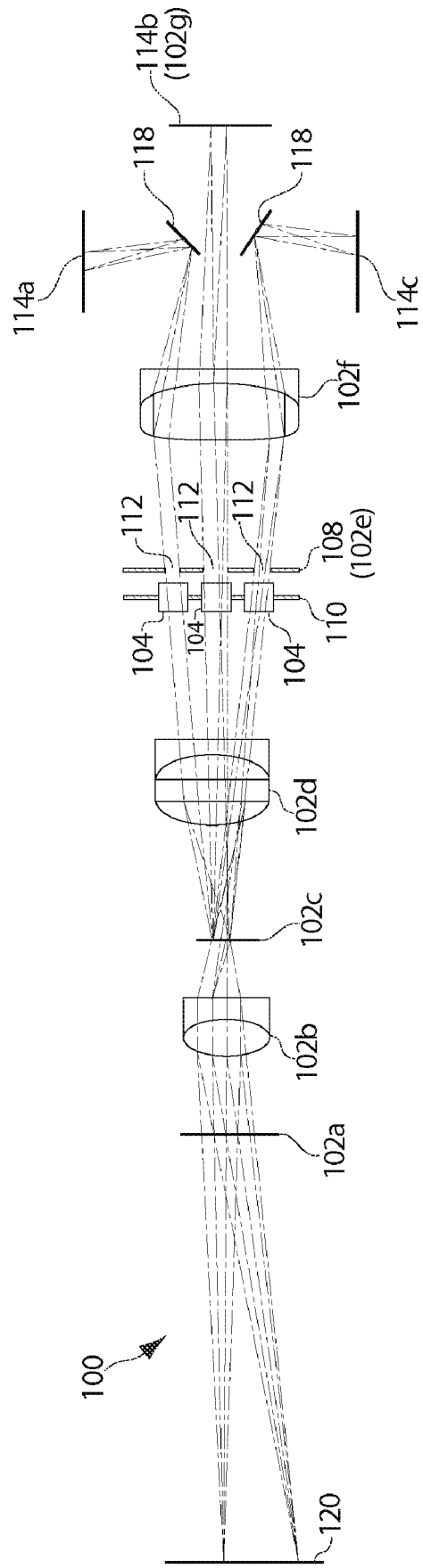
FIG. 1 shows an embodiment of an imaging system with a moving aperture component, a set of refocusing lenses, and a pupil splitting facility.

Referring to FIG. 1, a schematic diagram of an imaging system 100 in accordance with one preferred embodiment of the present disclosure is depicted, including various optional components. The imaging system 100 may include a primary optical facility 102, which may be employed in any kind of image processing system. In general, a primary optical facility refers herein to an optical system having one optical channel. Typically, this optical channel shares at least one lens, and has a shared image plane within the optical system, although in the following description, variations to this may be explicitly described or otherwise clear from the context. The imaging system 100 may include a single primary lens, a group of lenses, an object lens, mirror systems (including traditional mirrors, digital mirror systems, digital light processors, or the like), confocal mirrors, and any other optical facilities suitable for use with the systems described herein. The imaging system 100 may be used, for example in a stereoscopic or other multiple image camera system. Other optical facilities may include holographic optical elements or the like. In various configurations, the primary optical facility 102 may include one or more lenses, such as an object lens (or group of lenses) 102b, a field lens 102d, a relay lens 102f, and so forth. The object lens 102b may be located at or near an entrance pupil of the imaging system 100. The field lens 102d may be located at or near a first image plane 102c of the system 100. The relay lens 102f may relay bundles of light rays within the system 100. It will be understood that, while one embodiment is depicted in FIG. 1, numerous variations are possible. In addition, while some of the lenses (e.g., 102d and 102f) are depicted as doublets, these may also be single lenses.

The imaging system 100 may be designed for active wavefront sampling, which should be understood to encompass any technique used to sample a series or collection of optical data from an object or objects, such as the object 120 of FIG. 1, including optical data used to help detect two- or three-dimensional characteristics of an object, using optical data to detect motion, using optical data for velocimetry or object tracking, or the like. The object 120 may be located on a nominal object plane that is scanned by the imaging system 100, such as a system included in an imaging wand, camera or the like.

The imaging system 100 may include an aperture element 108, which may include any element or elements for selectively transmitting a portion of the optical signal transmitted through the primary optical facility 102. While depicted in a position between a field lens 102d and a relay lens 102f, it will be understood that the aperture element 108 may suitably be positioned in a variety of locations within or outside of the primary optical facility 102, such as in front of, inside or behind one of the lenses that serves as the primary optical facility 102. The aperture element 108 may include one or more apertures 112. In embodiments, the aperture element 108 may comprise any kind of aperture element, including a dynamic aperture, a moving plate, a moving aperture, an electronically controlled aperture, an electronic aperture, a shutter, a shuttering aperture, a variable aperture, an oscillating aperture, a controllable aperture, a rotating aperture, a flipping mirror, a rotating mirror, a digital light processor (DLP), or other similar component. The apertures 112 may be located in various positions, such as collinear/on-axis with the primary optical path of the imaging system, or in a paraxial location/off-axis. In embodiments the apertures 112 of the aperture element 108 may include multiple apertures 108 disposed in various configurations, such as a line of three apertures 112, an equilateral triangle of apertures 112, a pair of apertures 112, apertures 112 disposed in an "L" configuration, or the like. In embodiments, one of the apertures 112 may be located on a central axis of the imaging system 100. In one embodiment, a rotating aperture element 108 may rotate about a central axis of the imaging system 100, with three co-linear apertures 112 disposed therein, one of which is located on the central axis of the imaging system 100. It will be understood that any rotating element described herein may be adapted to rotate using any electro-mechanical or other means known in the art and suitable for use with the optical systems described herein. The other two apertures 112 of the aperture element 108 may be located in a line with the centrally located aperture 112, with the two side apertures each being spaced an equal distance from the center aperture 112. In other embodiments the apertures 112 may be arranged in various other configurations, such as triangles, "L" shapes, or the like. The three apertures 112 on the rotating aperture element 108 allow sampling of three distinct portions of the ray bundles passing through the primary optical facility 102. The aperture element 108 may allow active subsampling of a portion of the wavefront from the primary optical facility 102, such as a primary lens of an imaging system 100. One or more of the apertures 112 of the aperture element 108 may be located at a fixed position, either on the central axis of the imaging system 100 or at another position that is fixed or invariant relative to the imaging system 100. In embodiments the use of holographic optical elements may increase the offset of the side apertures, which may advantageously increase depth resolution or sensitivity of the imaging system 100.

One or more of the apertures 112 may serve as a fixed reference image for imaging processing. Thus, in one aspect, there is disclosed herein a three-dimensional imaging system that employs a multi-aperture element 108 in the primary optical path, having at least one invariant aperture location that establishes a reference image. The system may include a moving or active multi-aperture element 108. The system may include a splitting facility that supports three or more optical channels. The non-moving aperture may be located at a paraxial location or may be located on the center axis.

In another aspect, there is disclosed herein a three-dimensional imaging system having a three-aperture element 108 wherein the apertures 112 are collinear, i.e., linearly disposed with respect to one another. The three-aperture element 108 may be a moving component in which one or more of the apertures 112 move within the optical path. In alternative embodiments the aperture element 108 may include apertures disposed in a triangular (e.g., equilateral triangle) configuration or may include a pair of apertures disposed in a line, apertures disposed in an "L" shape (e.g., a right triangle), or the like.

The imaging system 100 may include one or more refocusing facilities 110, which should be understood to include any facilities for refocusing ray bundles, or an image or portion of an image, altering focus, adjusting focus or the like. Embodiments may include refocusing lenses, relay lenses, mirror systems or other optical facilities capable of relaying, coding, or refocusing light, including, as appropriate for a particular context, any of the optical facilities described in connection with the primary optical facility 102 above. In some embodiments, the refocusing facility 110 may include one or more meso-optical elements to expand depth of field for an optical path, such as glass cones or Wavefront Coding™ devices commercially available from CDM Optics, Inc. Meso-optical elements suitable for using with the systems disclosed herein are described, for example, in Meso-Optics Foundations and Applications by L. M. Soroko (November 1996), the entire contents of which are incorporated herein by reference. While these elements can expand the in-focus range for the associated optical path(s) and may permit capture of images at a distance that is different from the in-focus plane of the primary optical facility, it will be appreciated that the corresponding image obtained by a sensor may be encoded in a manner that requires a decoding algorithm or process to recover a sharp image from a ray bundle. Suitable decoding algorithms are known, and may be deployed in any image processing system(s) associated with a camera embodying the primary optical facility.

A refocusing facility 110 may support one or more refocusing elements 104 that consist of a plurality of refocusing lenses. The refocusing facility 110 and the aperture element 108 may be located at conjugate positions in the optical system 100 and in certain embodiments may be considered to be at substantially the same position within the system 100. For example, and not by way of limitation, the aperture element 108 and the refocusing facility 110 may be coplanar, such as by having each aperture surround a refocusing lens at a shared pupil of the optical facility. The refocusing facility 110 and aperture element 108 may rotate, so that they focus an image on one or more sensors when in the appropriate position. The refocusing facility 110 may rotate in the same direction as the rotating aperture element 108, in the opposite direction, at the same speed, and/or at a different speed. In embodiments, the rotation of the elements 110, 108 is controlled by a processor (not shown).

The imaging system 100 may include a sampling facility 118. The sampling facility 118 may include any type of facility that samples or redirecting a portion of the optical signal passing through the imaging system 100, such as a splitting facility, pupil splitter, pupil splitting facility, prism, splitter, mirror, pupil sampling facility, plurality of mirrors, partial mirror, filter, mirror with transparent element, a pair of mirrors with a space between them, or other such facility. In addition to sampling at the exit pupil (i.e., located outside the primary optical facility 102), it is possible to sample at an internal pupil of the primary optical facility 102. Referring still to FIG. 1, a sampling facility 118 may include a pair of mirrors for reflecting light in the imaging system 100 in different directions. The sampling facility 118 may include a number of mirrors position to reflect different ray bundles toward different sensors 114a, 114b and 114c. As depicted, a first sampling facility 118 may direct light toward a first side sensor 114a and a second sampling facility 118 may direct light toward a second side sensor 114c. A space may be provided between the two sampling facilities 118 that permits a coaxial (or paraxial) ray bundle to travel along the central axis of the imaging system 100 to a rear sensor 114b. It will be noted that, in the system of FIG. 1, each sampling facility 118 is positioned to receive a portion of the primary ray bundle selected by one of the apertures 112 of the aperture element 108. Each aperture 112 may also have a refocusing element 110 associated therewith at a conjugate location. In turn, each sensor 114a, 114b or 114c may receive a corresponding portion of the ray bundles from the primary optical facility 102, allowing separate processing of the different ray bundles.

It should be understood that various other arrangements may be provided for directing different ray bundles to different sensors 114. For example, a single mirror may be provided with a transmissive central element, e.g., a hole, to allow a portion of light to pass through to the rear sensor 114b. More generally, a variety of optical techniques including filters, splitters, mirrors, refractive and/or reflective elements, and the like, as well as various combinations of mechanical, electro-mechanical, and/or electrical shuttering may be usefully employed in the systems described herein.

The sensors 114 may include any sensors suitable for sensing a condition of optical energy, e.g., visible light, infrared energy, X-rays, ultraviolet light or other energy from any portion of the electromagnetic spectrum that might be transmitted through the primary optical facility 102. Sensors should be understood to include sensors capable of measuring the intensity of light, sensors for sensing a color of light, collections of sensors, e.g., RGB sensors, and the like. Sensors may include collections of sensors, such as one-, two-, or three-sensor collections, or larger collections of sensors, which may be arranged to receive different ray bundles or the same ray bundle. The imaging system 100 may direct different sampled ray bundles to different parts of the same sensor, thus forming a number of virtual sensors from a single sensor or pixel array. In one embodiment, three sensors 114a, 114b and 114c may be positioned as two side channels and one rear channel to receive different ray bundles from the primary optical facility 102, as selectively delivered through, e.g., the aperture element 108.

The imaging system 100 may include one or more image processing facilities (not shown), which should be understood to include any hardware, software, or other processing systems for processing image data. The image processing facility may include one or more individual sensors, as described herein, as well as a camera (still, motion picture, digital, video, or other camera), a computer, a machine vision system, an optical system, a reader, an object tracking device, a scope, or the like. An image processing facility may include one or more additional components, such as a processor, microprocessor, application specific integrated circuit, circuit, microchip, microcontroller, controller, hardware element, software, firmware, or other component for processing data, including image data. Image processing facilities should be understood to include and to enable various techniques for processing images, including techniques described herein and in the documents incorporated by reference herein for active wavefront sampling of optical images, techniques based on correlation of image data from different images, or other image processing techniques, e.g., decoding wavefront coded images, known to those of skill in the art. In one embodiment, data from the sensors 114a, 114b and 114c of FIG. 1 may be relayed to an image processing facility that is capable of processing the image data, such as to process images of the object 120, and resolve resulting image data into three-dimensional data. In embodiments, such an image processing facility may register different images from the imaging system 100, such as images from the apertures 112 of the aperture element 108, taking into account the location of the apertures 112 and the motion of the aperture element 108. For example, the image processing facility may take into account the fixed location of the central aperture 112 of a rotating aperture element 108, using image data from that aperture 112 as a fixed reference to assist with efficient image registration. Similarly, the relative positions of the side apertures 112 on the rotating aperture element 108 and their known relative positions, may allow efficient registration of the portions of the pupil of the imaging system 100 that are relayed through the respective side apertures 112 to the sensors 114a and 114c.

The imaging system may include one or more feedback facilities, which may encompass any components of an image processing facility for providing feedback to controllable elements associated with the image processing facility. In embodiments, a feedback facility may provide feedback to control, for example, the refocusing facility 110 (e.g., to control the rotation of a rotating refocusing facility 110), the aperture element 108 (e.g., to control rotation of a rotating aperture, such as in conjunction with a rotating refocusing facility 110), the location of the object 120 relative to the primary optical facility, the operation of electronic optical components, or any other controllable aspect of the imaging system 100.

The imaging system may include one or more relay optical facilities, such as the relay lens 102f of FIG. 1, which may encompass any component or element for maintaining the optical path of light between operative optical facilities. Embodiments may include various lenses for relaying an image, or a portion thereof, within an optical facility 102 or between a primary optical facility 102, refocusing lenses 104, an aperture 112, a pupil splitting facility 118 and/or one or more sensors 114.

The imaging system may include an electronic optical facility, which encompasses any electronic component that accomplishes one or more functions performed by any of the optical components or facilities described herein, such as transmitting, focusing, reflecting, diffracting, refracting or relaying light. Embodiments may include spinning or flipping mirrors, liquid crystal elements, digital light processors, or the like.

In one aspect, the disclosed system includes a three-dimensional imaging system having a single primary optical facility 102. The system may employ pupil splitting or pupil sampling in combination with multiple sensors, as shown and described with reference to FIG. 1. The system may employ a pair of splitting facilities 118, such as mirrors, in the primary optical path of the imaging system. Ray bundles may be split between a center path and at least one side path.

In general, it will be appreciated that numerous variations are possible to the system 100 depicted in FIG. 1. That is, certain components may be omitted, others may be added, and various components may be repositioned within the optical train. By way of example and not of limitation, a variety of aperture arrangements may be usefully employed with the systems described herein. For example, a camera using the system 100 may include an aperture element 108, but no refocusing facility 110, or may include an aperture element 108 and a refocusing facility 110 that includes one or more refocusing lenses but no optical wavefront coding elements, or may include an aperture element 108 and a refocusing facility 110 that includes one or more optical wavefront coding elements but no refocusing lenses. Different refocusing facilities 110 may also be used in combination. For example, the system 100 may include a first refocusing facility having refocusing lenses and a second refocusing facility having meso-optical elements, which may be in conjugate locations within the primary optical facility. All such variations that would be clear to one of ordinary skill in the art are intended to fall within the scope of this disclosure.

Figure 2:
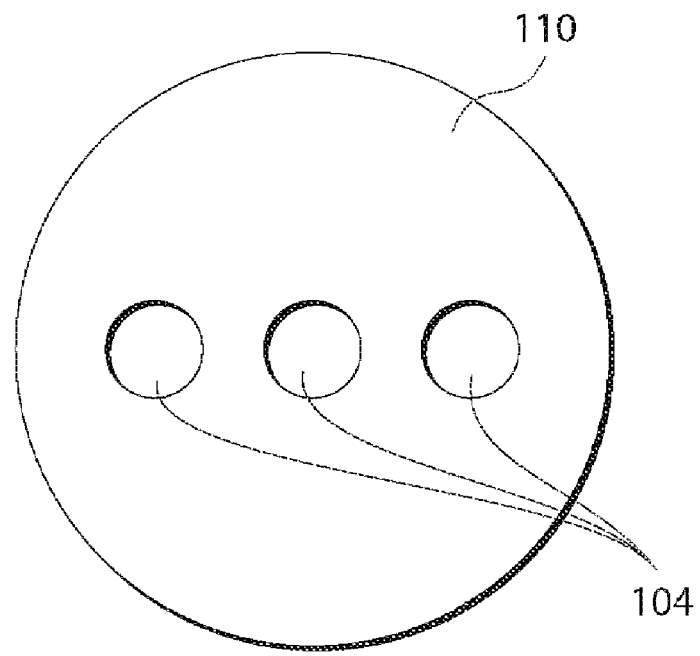
FIG. 2 shows an embodiment of refocusing facility.

FIG. 2 shows a view of an embodiment of the refocusing facility 110 as seen looking along the central axis of the imaging system 100, with refocusing lenses 104 disposed in a linear configuration, with a central refocusing lens 104 located at a central axis of the refocusing facility 110, so that it remains in a fixed, non-moving position during rotation of the refocusing facility 110. In embodiments one may create a rotating disk with a hole in the center where the non-moving center aperture is disposed.

Figure 3:
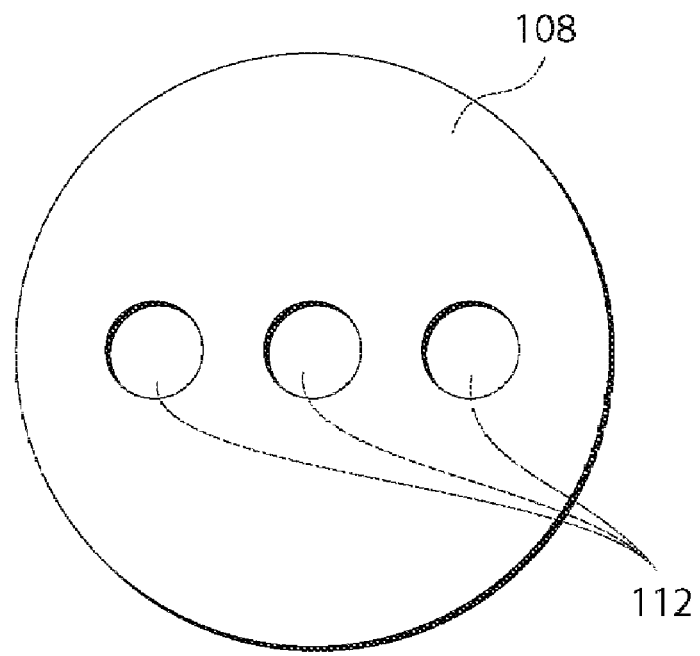
FIG. 3 shows an embodiment of a rotating aperture element.

FIG. 3 shows a view of the rotating aperture element 108 as seen along a central axis of the imaging system 100, with apertures 112 positioned in a linear configuration on the rotating aperture element 108, one of which is disposed at a central axis of the aperture element 108, so that the central aperture does not move when the aperture element 108 rotates. While the apertures 112 are shown as circular, it should be understood that in other embodiments non-circular apertures could be used, and an image processing facility may take advantage of irregular aperture shapes where possible in order to resolve image data for images that pass through such an irregular aperture. The linear arrangement of three refocusing lenses and three apertures as depicted in FIGS. 2 and 3 provide certain advantages. For example, the image transmitted through the center aperture 112 and center refocusing lens 104 can be used as a reference image in image processing, because it is located in the same position regardless of the motion of the rotating aperture 108. The side apertures 112 also move a fixed (and equal) distance when the aperture element 108 rotates, with the two side apertures moving equal distances in the same rotational direction. This known extent of rotation may simplify image processing of image data for data from the two side apertures. While in some embodiments the aperture plate 108 and the refocusing facility 110 may be separate facilities, it should be understood that in other embodiments the two may be combined into a single optical facility, such as with refocusing lenslets 104 located in or in close proximity to the apertures 112.

Figure 4:
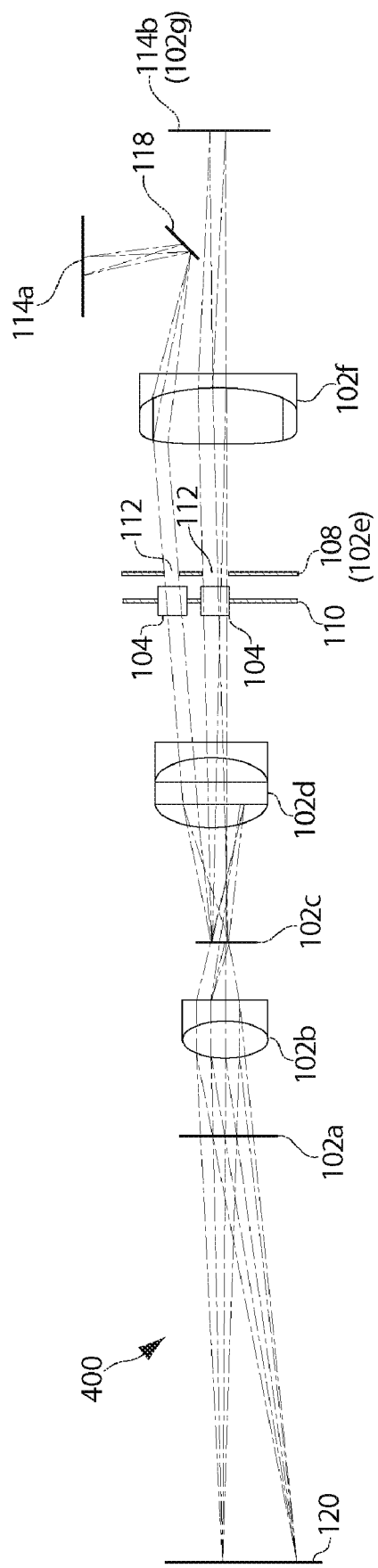
FIG. 4 shows an embodiment of an imaging system with two sensors.
Figure 5A:
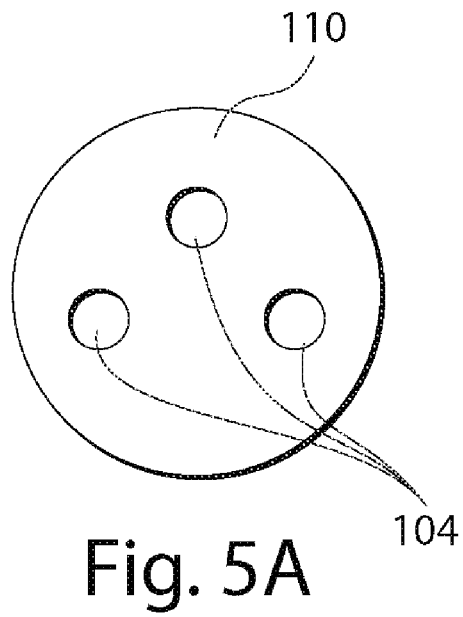
FIG. 5A through FIG. 5D, respectively, show an embodiment of a refocusing facility with three alternative aperture plate configurations.
Figure 5B:
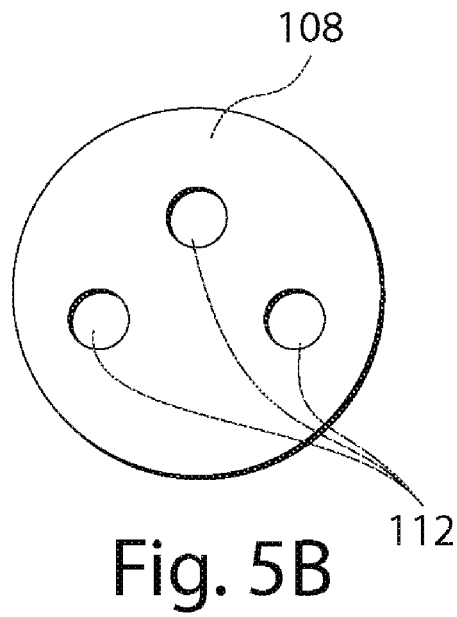
Figure 5C:
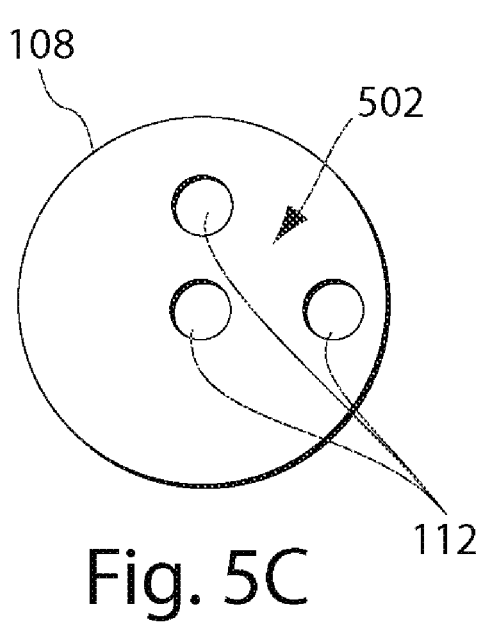
Figure 5D:
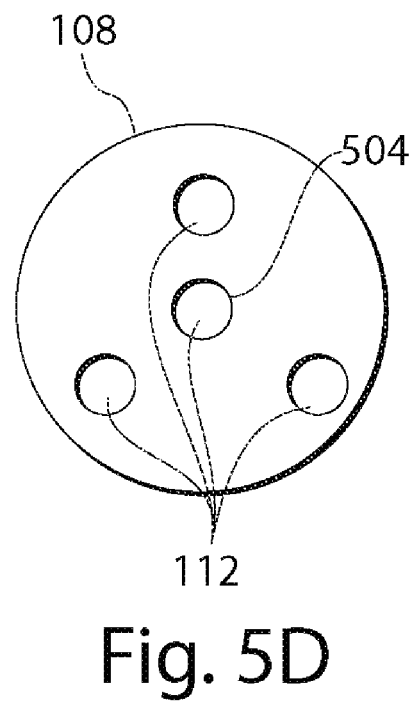

FIG. 4 shows an image processing system 400 similar to the image processing system 100 of FIG. 1, except that the image processing system 100 has two sensors 114a and 114b, in contrast to the three-sensor system of FIG. 1. The two sensors are configured to receive image portions from apertures 112 of the rotating aperture element 108, the image portions having been focused on the apertures by refocusing facility 110 in a manner similar to that described in connection with FIG. 1. In this case a single mirror 118 directs a ray bundle from a side aperture to the sensor 114, while the ray bundle from the central aperture 112 is allowed to pass directly to the rear sensor 114b. Optionally, the ray bundle from the central aperture 112 may be directed to a side aperture and the ray bundle from the side aperture may pass to a rear sensor. In such a system 400, an image processing facility would be configured to process data from the two sensors, optionally using data from the center aperture as a fixed reference image, facilitating efficient registration of images from the side aperture 112, since the motion of the side aperture relative to the center aperture is known.

FIG. 5 shows a number of alternate configurations for the refocusing facility 110, with refocusing lenses 104 disposed in a triangle (depicted here as an equilateral triangle, but optionally any form of triangle or other geometric configuration, such as a right angle (or "L" shape) 502 or a triangle combined with an additional central aperture 504 that is invariant in position upon rotation of the aperture plate 108). A corresponding rotating aperture element 108 includes apertures 112 disposed in a triangle, configured to correspond to the refocusing lenses 104. In embodiments, an imaging system similar to the system 100 would be used with these alternative embodiments of the refocusing facility 110 and the aperture element 108, but the splitting facility and sensors would be positioned to handle ray bundles from the triangular configuration of apertures 112, rather than being positioned to receive ray bundles along a line as depicted in FIG. 1. The known geometry of the apertures 112 would allow an image processing facility to process the relative motion of ray bundles based on the known relative motion of the apertures upon movement of the aperture element 108. In another embodiment, two apertures may be collinear with a center of the aperture element (relative to, e.g., a center axis of a primary optical facility), or spaced one-hundred and eighty degrees apart with respect to the center, while a third aperture is at a different angle with respect to the center and/or at a different distance from the center. The collinear apertures may be equally spaced or differently spaced from the center.

Figure 6:
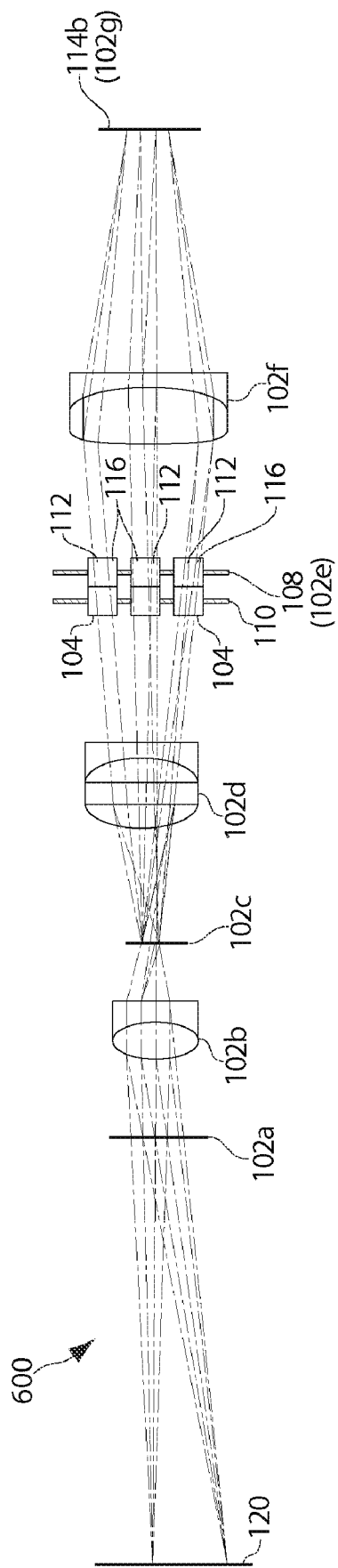
FIG. 6 shows a single-sensor embodiment of an imaging system.

FIG. 6 shows an imaging system 600 similar to the imaging system 100 of FIG. 1, except that the different ray bundles are relayed through the apertures of the aperture element 108 to a single sensor 602. In embodiments, the single sensor 602 may include different portions that are capable of responding differently to distinct ray bundles delivered thereto from each aperture 112, such as different pixels, e.g., with different color sensors on them. In other embodiments the light sensitive elements of the single sensor 602 may respond differently to different light spectra. For example, there may be a color filter array on the pixels. The filters can be tailored to the specific spectral bands filtered at, for example, each of the apertures 112. The single sensor can be a multi-spectral sensor (e.g., with R, G, B and IR pixels), or there can be multiple sensors among which one or more are RGB or multi-spectral. A sensor 602 can have different layers that capture light in different spectral bands, so that essentially every pixel location captures in all selected bands. Thus, in embodiments, the refocusing lenses 104 or the apertures 112 may be equipped with a set of filters 116, such as color or spectral bandpass filters, each of which filters light outside a particular color or frequency, so that different color images of the object 120 are delivered through the respective apertures 112 to the sensor 602, effectively rendering the single sensor 602 as the equivalent of three distinct sensors. In other embodiments, various regions of the sensor may be allocated to different ray bundles. Thus, a vision processing system can process data from the single sensor 602 in such an embodiment in a manner similar to the processing of image triplets as described in connection with FIG. 1. Thus in one aspect, the three-dimensional imaging system may include a multi-aperture component and bandpass filters 116 on one or more of the apertures.

It should also be understood that methods and systems are provided herein for three-dimensional imaging with a single primary optical facility 102, a multi-aperture element 108, and a single sensor. Embodiments include methods and systems for channeling rays through different apertures to different sections of the same sensor, e.g., particular pixels of the sensor. Embodiments include providing filters on the different apertures and using a single sensor to detect different wavelengths from the differently filtered apertures.

Figure 7:
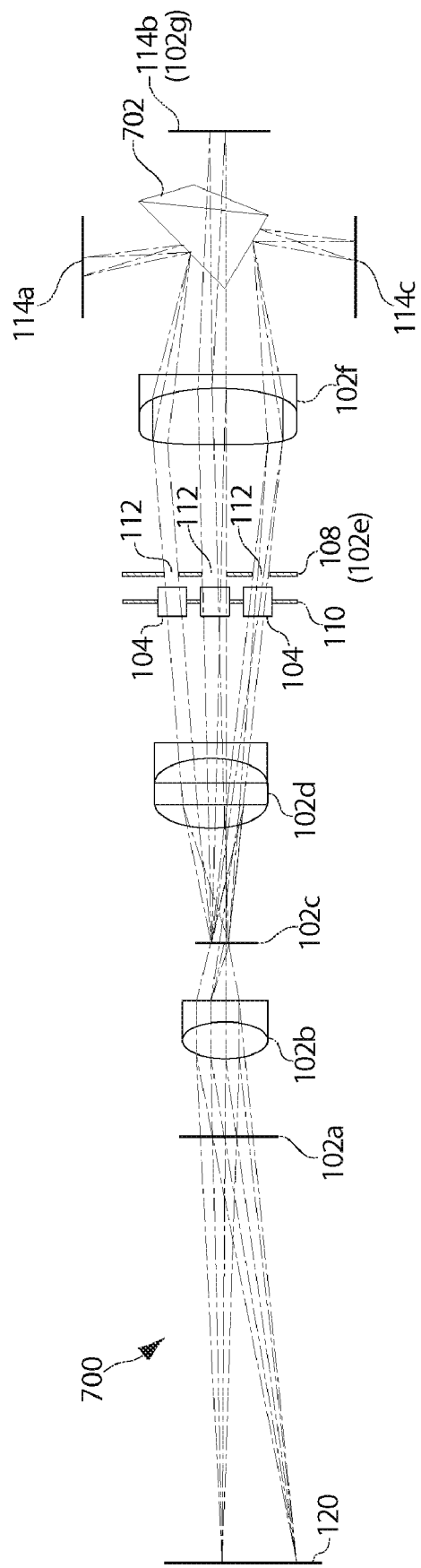
FIG. 7 shows an embodiment with a prism as a pupil splitting facility.

FIG. 7 shows an imaging system 700 similar to the imaging system 100 of FIG. 1, except that a prism 702 serves as a splitting facility 118, serving a similar function to the pair of mirrors depicted in connection with FIG. 1. The prism 702 reflects different ray bundles from the primary optical facility 102 to different sensors 114a, 114b and 114c, the ray bundles having been separated by a refocusing facility 110 and an aperture element 108 in conjugate positions similar to those described in connection with FIG. 1. If the components 110 and 108 are at conjugate locations (e.g. the aperture element 108 is at the entrance pupil plane), they may be synchronized such that if the refocusing facility 110 rotates, the aperture element 108 rotates accordingly. In addition, the refocusing lens 104 may have multiple lenslets (e.g., one at the center, and, for example, sixteen off axis) in which case a rotating aperture element 108 at any pupil position (102*a*, 102*e*, and somewhere between 102*f* and 118/702) may select which lenslets actually let light through. In another optional embodiment, the refocusing facility 110 may be replaced with a rotating radial slit, and the aperture element 108 may be replaced with an annular mask at a pupil (e.g., at 102*a*, 102*e*, and somewhere between 102*f* and 118/702). The intersection of these two would define an aperture shape and location. More generally, it should be understood that while the prism 702 and the pair of mirrors of FIG. 1 represent two possible embodiments, any other kind of optical facility described herein may be configured to deliver different portions of the pupil of the image to the respective sensors, and all such embodiments are encompassed herein. As one example, the prism 702 may be replaced with two mirrors or prisms leaving an open center channel for the center ray bundle.

Figure 8:
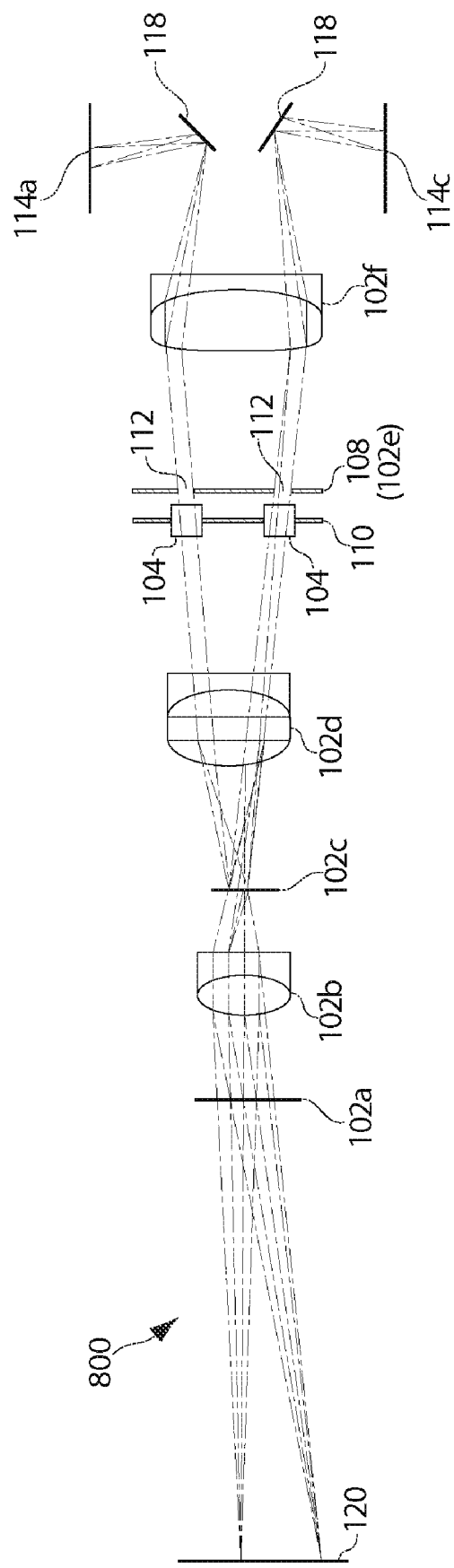
FIG. 8 shows an embodiment of an imaging system with two side-channel sensors.

FIG. 8 shows an imaging system 800 with two sensors 114*a* and 114*c*, in this case receiving ray bundles from a pair of mirrors 118 that in turn receive ray bundles from a pair of apertures 112 located on an aperture element 108. Various other two-sensor embodiments are possible and are encompassed herein.

Figure 9A:
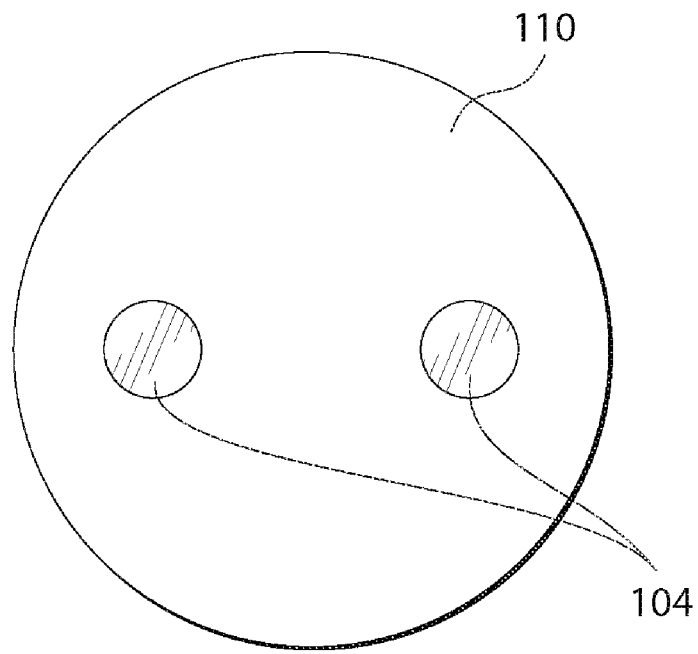
FIG. 9A and FIG. 9B, respectively, show an embodiment of a refocusing facility and a corresponding aperture plate.
Figure 9B:
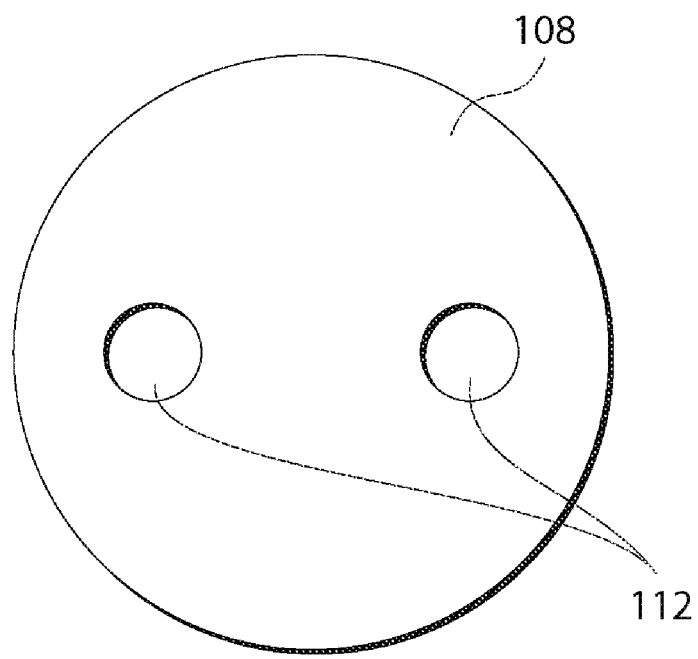

FIG. 9 shows a refocusing facility 110 with a pair of refocusing lenses 104, as well as an aperture element 108 with a corresponding pair of apertures 112, suitable for a two-sensor embodiment such as the imaging system 800 of FIG. 8.

Figure 10:
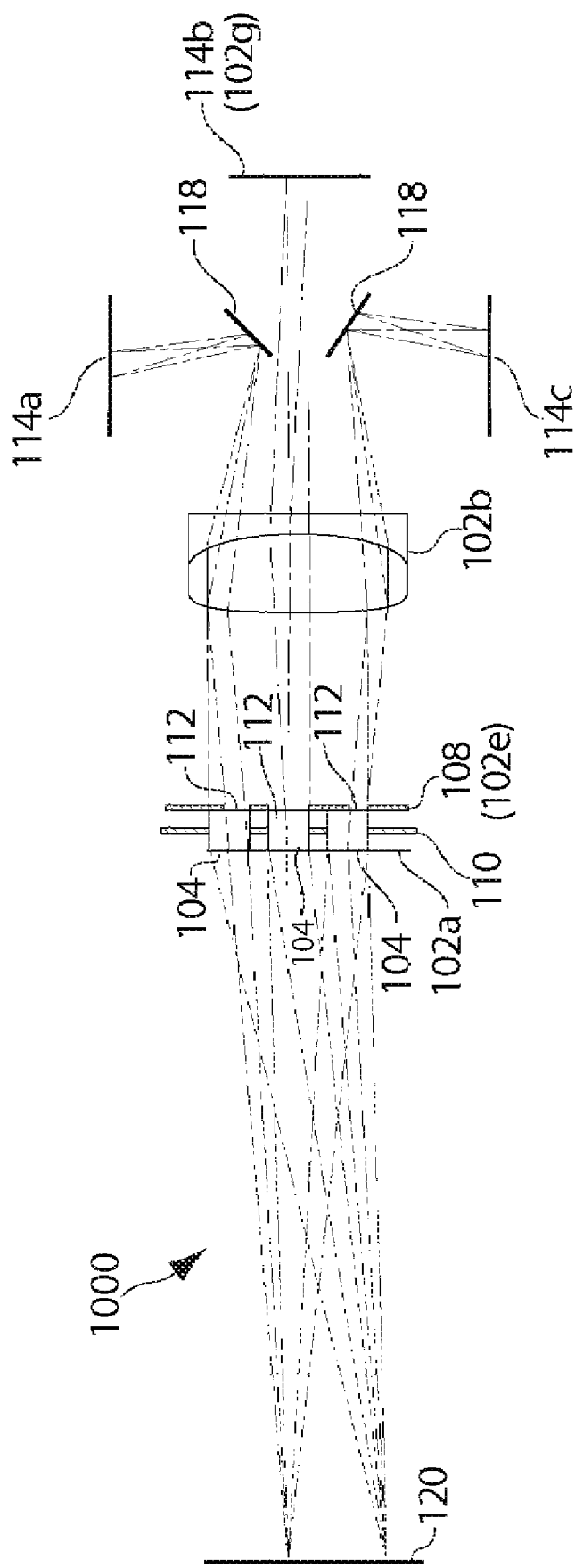
FIG. 10 shows an embodiment of an imaging system with a refocusing facility and a moving aperture element disposed in front of a primary optical lens.

FIG. 10 shows an imaging system 1000 similar to the imaging system 100 of FIG. 1, but in the embodiment depicted in FIG. 10 the rotating aperture element 108 and the refocusing facility 110 with the refocusing lenses 104 are integrated as a single facility and are disposed at or in close proximity to the entrance pupil 102*a* between the object 120 and the primary optical facility 102, which in this case only shows a primary lens 102*b* (but could have various relay lenses or the like), so that ray bundles are sampled before entering the primary optical facility 102. It should be thus understood that various configurations of the primary optical facility 102, the rotating aperture element 108 and the refocusing facility 110 are intended to be encompassed herein.

Figure 11:
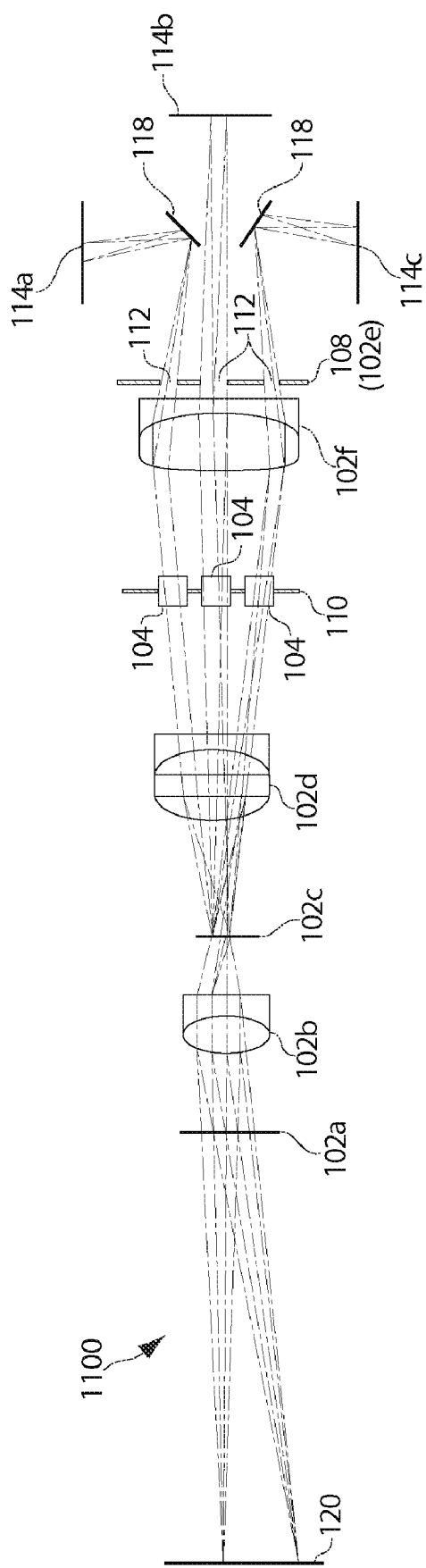
FIG. 11 shows an embodiment of an imaging system with a refocusing facility in front of a primary optical lens and a moving aperture component behind the primary optical lens.

FIG. 11 shows an imaging system 1100 similar to the imaging system 100 of FIG. 1 and the imaging system 1000 of FIG. 10, but in the embodiment depicted in FIG. 11 the rotating aperture element 108 and the refocusing facility 110 are disposed on opposite sides of a relay lens 102*b* within the primary optical facility 102, so that ray bundles are refocused before entering the lens 102*f*, then sampled by different apertures of the rotating aperture element 108 after exiting the primary optical facility. Again, it should be understood that various configurations of the primary optical facility 102, the rotating aperture element 108 and the refocusing facility 110 are encompassed herein.

Figure 12:
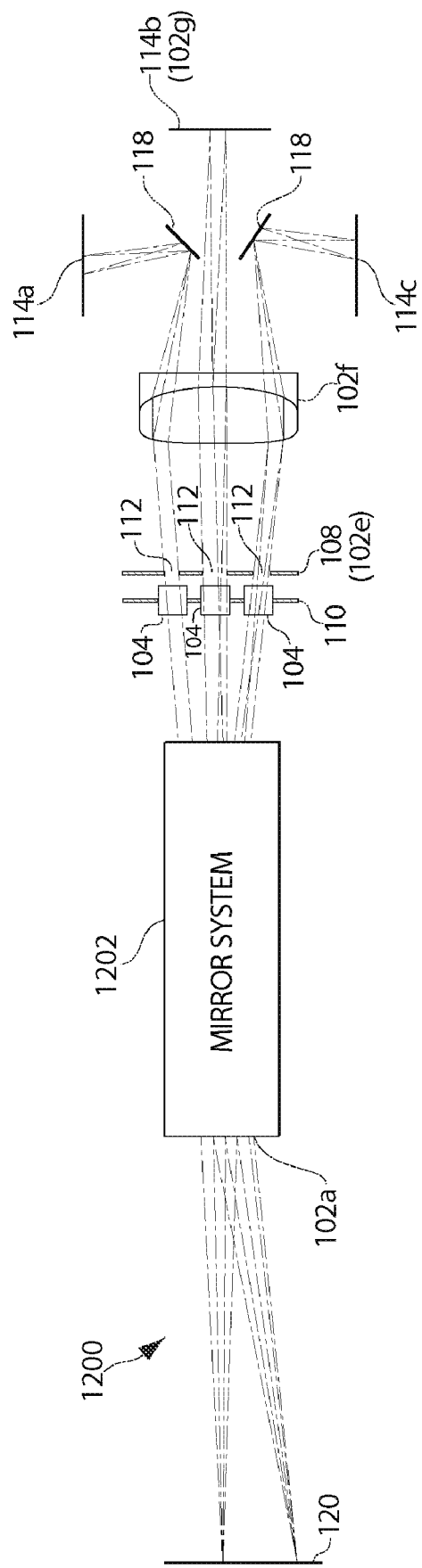
FIG. 12 shows an embodiment of an imaging system with a set of mirrors serving as a primary optical facility.

FIG. 12 shows an imaging system 1200 similar to the imaging system 100 of FIG. 1, except that the primary optical facility 102 may include a mirror system 1202, which may include a set of mirrors that are configured to reflect light from the object 120 to the refocusing facility 110 and in turn through the apertures 112 of the rotating aperture element 108. Various alternative embodiments may be envisioned for the primary optical facility 102, encompassing any type of optical facility contemplated herein, or components or combinations thereof. More generally, while depicted as a mirror system 1202 that reflects and redirect light prior to entering an aperture element 108 and the like, it will be understood that one or more mirrors may be positioned in numerous locations within the optical train depicted in, e.g., FIG. 1, and all such variations are intended to fall within the scope of this disclosure. For example, various refractive or filtering optical elements discussed above may be replaced with or supplemented by mirrors within the systems described herein.

Figure 13:
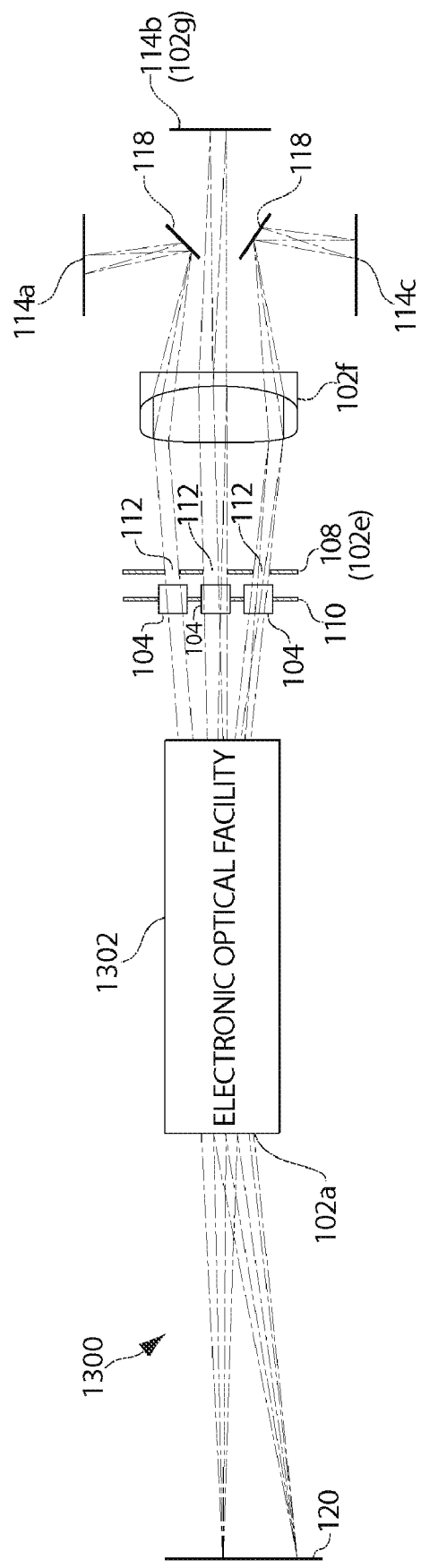
FIG. 13 shows an embodiment of an imaging system with an electronic optical component.

FIG. 13 shows an imaging system 1300 similar to the imaging system 100 of FIG. 1, except that the primary optical facility 102 may include an electronic optical facility 1302, shown in block diagram format, where the electronic optical facility 1302 is configured to deliver light from the object 120 to the refocusing facility 110 and in turn through the apertures 112 of the rotating aperture element 108. In embodiments the electronic optical facility 1302 may further encompass, or substitute for, the refocusing facility 110 and/or the aperture element 108. Various alternative embodiments may be envisioned for the electronic optical facility 1302, encompassing any type of electronic optical facility contemplated herein, or components or combinations thereof, such as spinning or flipping mirrors, digital light processors, liquid crystal-based components, or the like. In embodiments the electronic optical facility may be located at an entrance pupil 102*a* of the system 1300. More generally, various electronic or electromechanical optical elements may be used in various locations within the optical train depicted in, e.g., FIG. 1, and all such embodiments are intended to fall within the scope of this disclosure.

Figure 14:
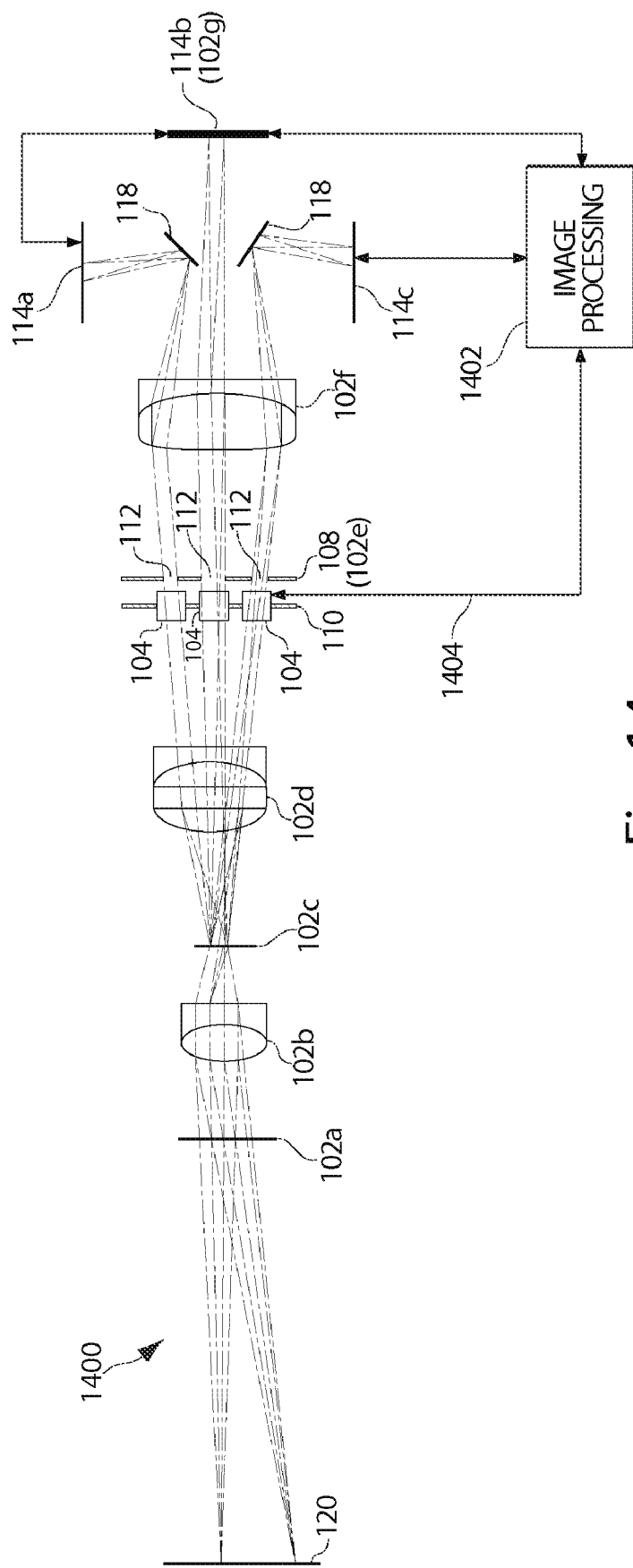
FIG. 14 shows an imaging system with an associated image processing facility and including a feedback facility for providing feedback control to components of the imaging system.

FIG. 14 shows an imaging system 1400 similar to the imaging system 100 of FIG. 1, in this case showing an image processing facility 1402 associated with the sensors 114*a*, 114*b* and 114*c* for receiving and processing image data from the ray bundles sampled by the pupil sampling system of the imaging system 1400, which includes the rotating aperture element 108 and the refocusing facility 110, which deliver ray bundles to the splitting facility 118, a set of mirrors similar to those depicted in connection with FIG. 1. In this case the image processing facility includes a feedback facility 1404, providing feedback control of the rotating aperture element 108 and the rotating refocusing facility 110 under control of the image processing facility 1402, such as to control the sampling of images in order to achieve various processing techniques, including the techniques described herein and techniques described in the documents incorporated by reference herein.

A three-dimensional imaging system as described herein may include a facility for separately handling distinct bundles of light rays from a single primary optical facility 102, such as a primary optical lens or set of lenses. The facility may include a refocusing facility 110, a moving aperture 108, a splitting facility 118, a combination of the foregoing, or an alternative optical arrangement that similarly handles distinct bundles or portions of image data.

The moving (e.g., rotating) aperture element 108 in the primary optical path may have an off-axis aperture or an on-axis aperture with a non-standard aperture shape, such as a slit. The aperture element 108 may also, or instead, include multiple moving or rotating plates. In addition, the apertures 112 in each of the one or more moving components may have various shapes. For example, to rotating disks, each having an elongated slit passing through or near its center, may be jointly controlled to provide an aperture at an arbitrary, programmable location within the optical path.

In certain preferred embodiments, provided herein are methods and systems for three-dimensional imaging using a rotating, multi-aperture plate 108 in the primary optical path, with feedback control of the rotating plate 108 through a feedback facility 1504.

Provided herein are methods and systems for three-dimensional imaging using a moving (e.g., rotating), multi-aperture element 108 at a pupil of the primary optical path. In embodiments the moving aperture component may be disposed either behind, in front of, or within a primary optical facility 102, such as a primary lens. Embodiments may include relay lenses 1402. Other embodiments may include intermediate optical facilities, or refocusing lenses 110, in front of the primary optical facility.

It should be understood that certain preferred embodiments may include one or more masking elements (e.g., a rotating shutter) for masking a portion of the primary bundle of light rays in the optical path of an imaging system.

In embodiments, the methods and systems described herein can be used for other purposes, such as for correcting aberrations. Thus, methods and systems include a three (or more) sensor system for correcting aberrations in image data.

It may noted that in various embodiments described herein, methods and systems are provided for three-dimensional imaging in which separate ray bundles are sampled, but the sampled portions of a primary ray bundle share at least one optical element after the sampling. It should also be noted that in certain embodiments herein are methods and systems are provided for three-dimensional imaging with pupil sampling at one pupil and relevant pupil splitting at another pupil of the imaging system.

It may be noted that provided herein are methods and systems that use three image sensors that record three independent perspectives through a single lens, using pupil sampling or pupil splitting. In embodiments, three sensors and a single lens are used. Unlike a typical triplet imaging system, which has three sensors located in a triangular pattern (but may have various other patterns) about a center position, in certain preferred embodiments the methods and systems disclosed herein may locate the third sensor between the two other sensors. This allows the third sensor to record object feature positions that are ideally an average of the positions recorded by the sensors to the left and to the right. This third sensor records an object position to which the other object images can be referenced. It provides a reference independent of object depth. This greatly simplifies registration of image data taken in time with a moving object and/or camera.

In embodiments, images from the three sensors are processed using a unique image registration technique that takes advantage of the third imaging sensor's location. Because the displacement of object features imaged by the third sensor are ideally an average of feature positions recorded by the left and right sensors, image registration between the third (center) sensor and the left sensor indicates a feature displacement equal in distance but opposite in direction to that of the imaged feature displacement between the center sensor and the right sensor. By changing the sign of the displacement direction of the registration between two sensors, a more accurate measure of image disparity can be found by combining the registration among the data from the different sensors. Additionally, there is the capability to use spatio-temporal processing methods, which may be more accurate.

Thus, various embodiments disclosed herein include methods and systems for combined pupil sampling by splitting the pupil of the primary optical system into one on-axis and multiple off-axis apertures for instantaneous capture of multiple images in the same spectral band by a monocular camera for three-dimensional imaging of moving objects. Thus, embodiments involve pupil sampling by a single moving/non-moving aperture element such as to image stationary scenes. Multiple images instantaneously captured in the same spectral band at different aperture locations on different sensors are made possible by combining pupil sampling done by a moving aperture mask (e.g., three collinear apertures) with pupil splitting by a set of stationary mirrors or prisms. Under this condition, after pupil sampling the individual rays share the same optical elements. This allows the implementation of a freely moving sampling aperture 112 and associated elements) with a stationary splitting facility (e.g., mirrors, prism, or the like). One aperture at the center and one or more at an off-axis location are used for capturing three-dimensional images of moving objects. Rays passing through the different apertures share the optics before and after pupil sampling and are have different optical paths before sampling.

Thus, the various methods and systems disclosed herein enable using a moving aperture with pupil splitting. In various embodiments the optical path of a single lens can be split into three regions and sent to separate sensors. A moving aperture plate with three aperture openings can be used to control the parts of the lens being used for imaging. By rotating the mask, the perspective seen by each of the sensors changes. The advantage of this arrangement, in addition to the advantages of using an offset rotating aperture, is that images from the three sensors can be used to acquire three-dimensional information. Thus, multiple images taken in time are not required to resolve the three-dimensional shape of an object. This greatly simplifies three-dimensional processing when wavefront imaging is used to image a moving object.

In other embodiments, methods and systems disclosed herein also include methods and systems to support off-axis optical wavefront and defocus blur sampling referenced to an on-axis image. In embodiments, an imaging system may assist in capturing imaging data for images of three-dimensional surfaces by quantitatively measuring the defocus blur size of the images. In particular, by pupil sampling with one or more off-axis apertures (e.g., the off-axis apertures disclosed in connection with FIG. 3), it is possible to recover data relative not only to the amount of defocus (D) of an image, but also data relative to the center of a blur spot $(x_o, y_o)$. The "blur spot" refers to the diameter of the circle an imaged object feature would make if an aperture offset from the lens axis were rotated about the lens axis. The aforementioned pupil sampling gives three unknowns to recover for every measured point: $x_o(i)$, $y_o(i)$, $D(i)$. However, the problem can be reduced to only one unknown (the amount of defocus, $D(i)$) by capturing an on axis image with the help of the aperture 112 that is centered on the optical axis of the imaging system 100. This center image (as a reference) also facilitates fusing information together from images captured at multiple off-axis aperture positions. Furthermore, because this center image does not encode depth into the image location of object features, it also allows camera path recovery and stitching together or registering images of surfaces measured at different camera positions. Thus, a center-imaging sensor in a stereo imaging system provides a reference image. While this concept has been disclosed in connection with the imaging system 100 and other imaging systems disclosed herein, such as including a rotating aperture system, it should be understood that using a center image as a reference image and an off-axis image for optical wavefront and blur sampling in reference to that image can be used in any multi-sensor imaging system such as in a triplet imaging or wavefront system.

Figure 15:
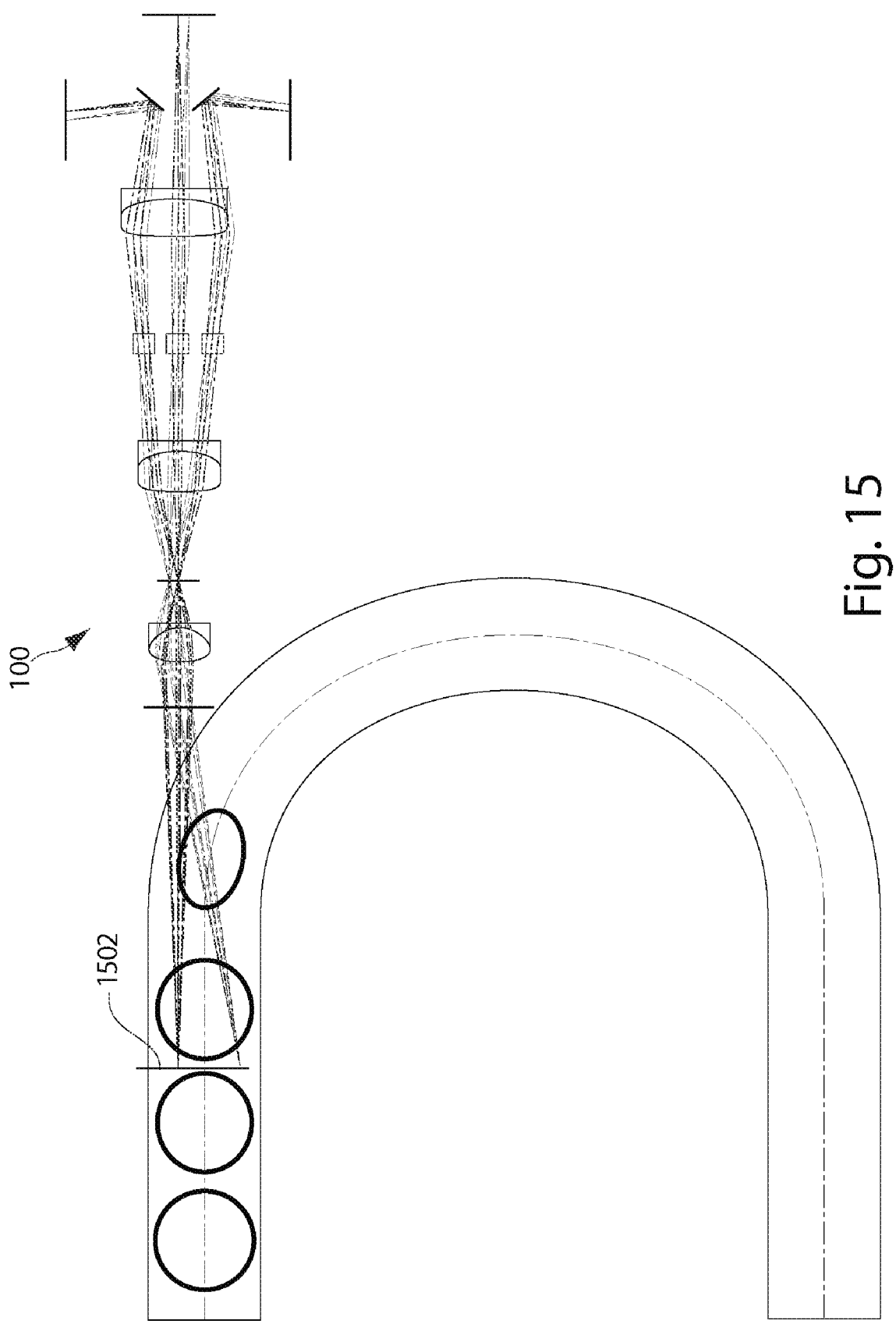
FIG. 15 shows a technique for viewing narrow areas with an imaging system.

Referring to FIG. 15, a technique for orienting the pupil of an imaging system, such as an imaging wand, relative to a narrow area of an object is provided. In embodiments of imaging systems, the relative orientation of pupil sampling apertures in an imaging system, such as the imaging system 100 or another imaging system, may be adjusted to minimize occlusion when capturing interproximal surfaces. In particular, apertures can be disposed off-axis to be aligned with the orientation of the interproximal surface line. For example, when imaging the gap between teeth, such as using a dental imaging wand, the sensors can be aligned parallel to the gap such that all three cameras are able to observe down into the gap region. If they were located perpendicular to the gap, only one of the sensors could be located to look down into the gap. The other sensors would observe the gap from an angle and would therefore only see one side of the gap or the other. Thus, in order to see into narrow areas (e.g. the interproximal gap 1502) and capture multiple (e.g., three) images without occlusion, the layout of the three apertures is aligned to the most likely relative orientation of the wand to the object. In another aspect, an additional mirror or other optical facility may be provided to dynamically or controllably re-align the ray bundles as they enter the imaging system 100.

Figure 16:
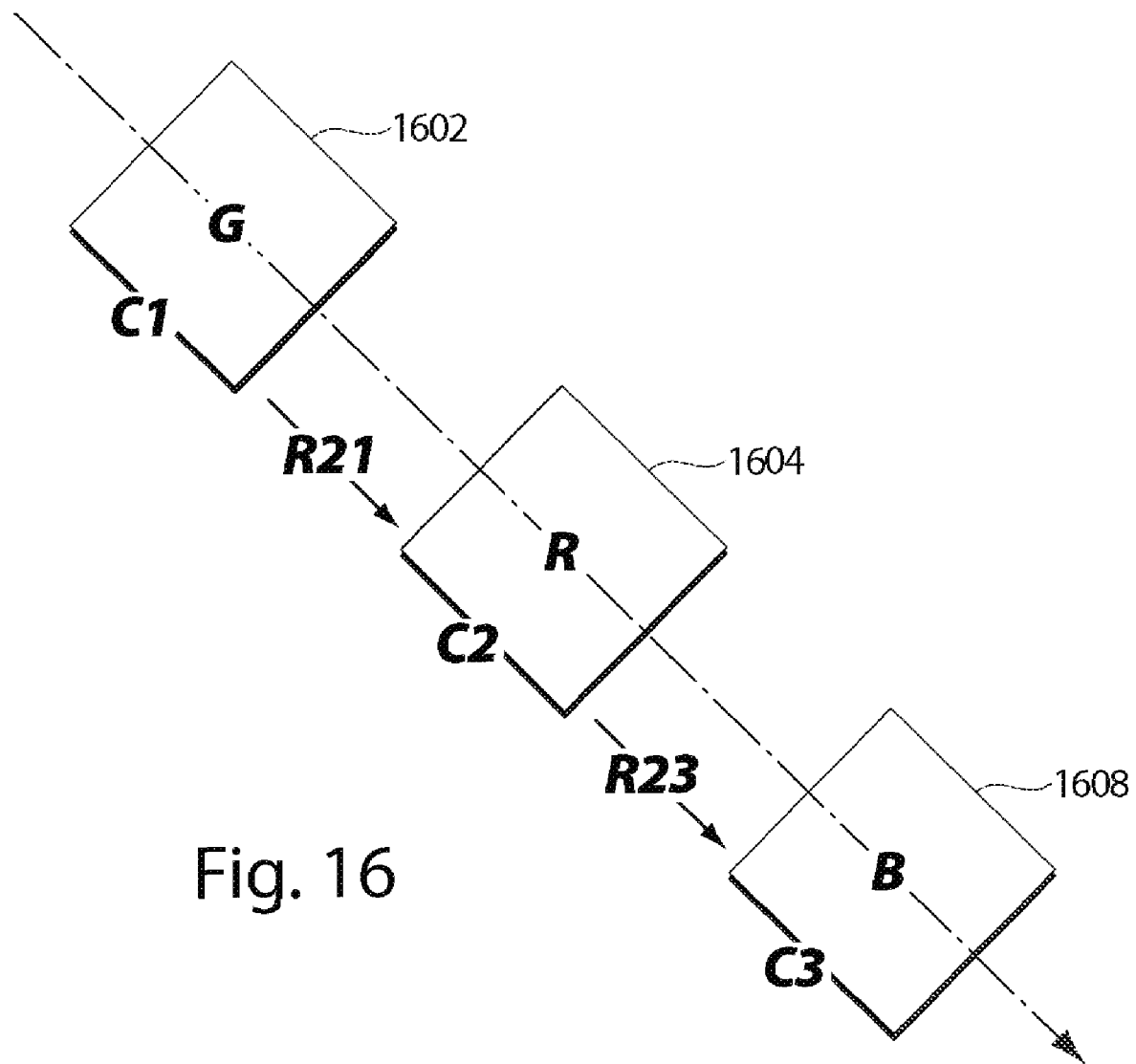
FIG. 16 is a schematic diagram reflecting a set of images taken by cameras in an image triplet processing technique.

Referring to FIG. 16, in other embodiments the methods and systems provided herein enable image triplet processing based on correlation disparity. In particular robust, high spatial resolution, and accurate image triplet processing can be performed by taking advantage of known (e.g. given by epipolar lines) disparity directions, and building on how patterns in a correlation plane are preserved when image features move across the frame. For example, referring to FIG. 16, if images from three cameras 1602, 1604 and 1608, (such as cameras sensitive to red, green and blue (RGB) images, or other sensors) are aligned collinearly, disparity detection (for example by correlation) can be performed on the R-to-G, and the 180 degree rotated R-to-B correlation fields. In this way, the R-to-G and the rotated R-to-B true correlation peaks will enhance each other, allowing smaller interrogation (search area) size to be used in the center (R) channel. This may improve robustness and/or spatial resolution. Accuracy may also be improved by enforcing correlation peak symmetry after identifying the signal peak, and performing the "backward" correlation (R-to-G and G-to-R, etc.). Thus, in an embodiment such as the embodiment of FIG. 1, registering the center image with the image from either the left or the right image takes advantage of the fact that the registered displacement of the same object feature with the opposite sensor is equidistant along a line parallel to the placement of the sensors but in the opposite direction. By reversing the sign of one of the image registrations relative to the center sensor, it can be combined with the registration of the center sensor to the opposite sensor. This provides improved accuracy and robustness to the processing of image triplets.

In embodiments, images from the three sensors are processed using a unique correlation technique that takes advantage of the third imaging sensor's location. Because the displacement of object features imaged by the third sensor are an average of feature positions recorded by the left and right sensors, image registration between the third (center) sensor and the left sensor indicates a feature displacement equal in distance but opposite in direction to that of the imaged feature displacement between the center sensor and the right sensor. By changing the sign of the displacement direction of the registration between two sensors, a more accurate measure of image disparity can be found by combining the registration between the center sensor and either the left or right sensor and the opposite sensor (right or left sensor).

In embodiments, the methods and systems disclosed herein may combine multi-view imaging with estimating the amount of defocus (blur) at the image plane. To avoid the contaminating effect of optical aberrations in capturing depth-related image motion, the system may be designed such that at a nominal working distance the object is placed in between the in-focus/reference plane of the primary optical system 102. This may result in a blurring or low pass filtering effect on the images captured through the on-axis and off-axis apertures. In order to compensate for this, and to increase optical resolution at the nominal working distance a set of refocusing lenslets may be used on the apertures to move the ray bundles back to focus without altering the path of the chief ray. Additionally, these lenses can also compensate or correct for some aperture-location-specific optical artifacts, to improve the resolving power of the optics (e.g. Modulation Transfer Function) for every aperture. However, even if the images are now in-focus at the nominal distance, narrow depth-of-field is still a problem. This can be addressed by applying other special optical elements on the apertures, such as a meso-optical element (a diffractive optical element that increases depth-of-field), or a wavefront coding element. Using these requires a special preprocessing step on the images to decode the depth or focus related data, and to construct an image that has larger depth-of-field than if it were acquired without these elements.

While the invention has been described in connection with certain preferred embodiments, other embodiments may be understood by those of ordinary skill in the art and are encompassed herein.

What is claim is:

1. A device comprising an aperture element positioned within a primary optical facility having a center axis, the aperture element including three apertures positioned collinearly, each one of the apertures selectively transmitting a portion of an optical wavefront of the primary optical facility, thereby providing three optical channels, and a center one of the apertures positioned on the center axis.

2. The device of claim 1 wherein the three apertures are substantially equally spaced apart.

3. The device of claim 1 wherein the aperture element includes one or more of a moving plate, an electronic aperture, a shutter, a shuttering aperture, an oscillating aperture, a flipping mirror, a rotating mirror, and a digital light processor.

4. The device of claim 1 wherein the aperture element is adapted to rotate on the center axis.

5. The device of claim 1 further comprising a refocusing facility having three refocusing elements located at conjugate positions to the three apertures within the primary optical facility.

6. The device of claim 5 wherein the refocusing facility is adapted to rotate on the center axis.

7. The device of claim 5 wherein the aperture element is adapted to rotate on the center axis.

8. The device of claim 7 wherein the refocusing facility is adapted to rotate in an opposite direction from the aperture element.

9. The device of claim 1 further comprising three optical sensors positioned to capture data from each of the three optical channels.

10. The device of claim 9 wherein each one of the three optical sensors includes a collection of sensors to acquire RGB data.

11. The device of claim 9 further comprising a sampling facility that redirects the three optical channels to the three optical sensors.

12. The device of claim 11 wherein the sampling facility includes two mirrors separated by a space that passes a center one of the optical channels corresponding to the center one of the apertures.

13. The device of claim 11 wherein the sampling facility includes three mirrors.

14. The device of claim 11 wherein the sampling facility includes at least one prism.

15. The device of claim 14 wherein the at least one prism includes a prism having a hole that passes a center one of the optical channels corresponding to the center one of the apertures.

16. A device comprising a refocusing facility positioned within a primary optical facility having a center axis, the refocusing facility including three refocusing elements positioned collinearly and substantially equally spaced, each one of the three refocusing elements refocusing a portion of an optical wavefront of the primary optical facility, and a center one of the refocusing elements positioned on the center axis.

17. The device of claim 16 wherein the refocusing facility is adapted to rotate on the center axis.

18. The device of claim 16 wherein the refocusing elements include at least one mirror.

19. The device of claim 16 wherein the refocusing elements include at least one lens.

20. The device of claim 16 wherein the refocusing elements include at least one meso-optical element.

21. The device of claim 16 further comprising three optical sensors positioned to capture data from each of the three optical channels.

22. The device of claim 21 wherein each one of the three optical sensors includes a collection of sensors to acquire RGB data.

23. A method of processing images from sensors comprising:

receiving the output of three optical sensors of an imaging system, the three optical sensors including a center sensor that captures data from a center channel of an optical path and two side sensors, each side sensor having an equal displacement with respect to image motion within the optical path;

changing a sign of displacement direction of a registration between two of the sensors; and combining a registration between the center sensor and the two side sensors.

* * * * *

UNITED STATES PATENT AND TRADEMARK OFFICE
CERTIFICATE OF CORRECTION

PATENT NO. : 7,646,550 B2 Page 1 of 1
APPLICATION NO. : 11/530420
DATED : January 12, 2010
INVENTOR(S) : Rohaly et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 765 days.

Signed and Sealed this

Sixteenth Day of November, 2010

David J. Kappos
*Director of the United States Patent and Trademark Office*